United States Patent [19]

Skuballa et al.

[11] Patent Number: 5,414,016
[45] Date of Patent: May 9, 1995

[54] NEW LEUKOTRIENE-B4 DERIVATIVES, PROCESS FOR THEIR PRODUCTION AND THEIR USE AS PHARMACEUTICAL AGENTS

[75] Inventors: Werner Skuballa; Bernd Buchmann; Josef Heindl; Wolfgang Fröhlich; Roland Ekerdt; Claudia Giesen, all of Berlin, Germany

[73] Assignee: Schering Aktiengesellschaft, Berlin and Bergkamen, Germany

[21] Appl. No.: 259,111

[22] Filed: Jun. 13, 1994

Related U.S. Application Data

[63] Continuation of Ser. No. 961,728, Jan. 12, 1993, abandoned.

[30] Foreign Application Priority Data

Mar. 12, 1991 [DE] Germany ............... 41 08 351.2

[51] Int. Cl.6 ................. C07C 405/00; A61K 31/557
[52] U.S. Cl. ..................... 514/460; 514/530; 514/573; 514/729; 549/273; 560/121; 560/231; 562/503; 564/189; 568/838
[58] Field of Search ............. 560/121, 231; 562/503; 568/838; 549/273; 514/460, 530, 573, 729

[56] References Cited

FOREIGN PATENT DOCUMENTS 0103445 3/1984 European Pat. Off. .
3917597 11/1990 Germany .

OTHER PUBLICATIONS

Vth International Conference on Prostaglandins, Florence (May 18–21, 1982), P. Borgeat et al.: "Inhibition of the synthesis of leukotriene B4 (LTB4) in human leukocytes by hydroxy–eicosatetraenoic acids", II.

Primary Examiner—Robert Gerstl
Attorney, Agent, or Firm—Millen, White, Zelano & Branigan

[57] ABSTRACT

Leukotriene-$B_4$ derivatives of formula I

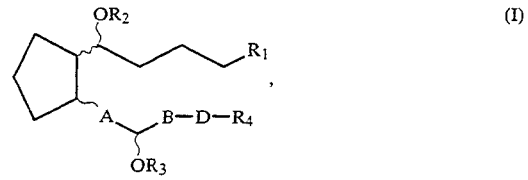

are described, in which $R^1$ means $CH_2OH$, $CH_3$, $CF_3$, $COOR^5$, $CONR^6R^7$, or $R^1$ together with $R^2$ means a carbonyl group, $R^4$ symbolizes H, $C_1$-$C_{10}$ alkyl optionally substituted, $C_3$-$C_{10}$ cycloalkyl, $C_6$-$C_{10}$ aryl radical optionally substituted, or a 5-6-membered aromatic heterocyclic ring, A symbolizes a trans, trans-CH=CH—CH=CH, a —$CH_2CH_2$—CH=CH— or a tetramethylene group, B symbolizes a $C_1$-$C_{10}$ alkylene group, which optionally can be substituted by fluorine or the group

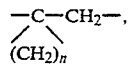

D can mean a direct bond, oxygen, sulfur, —C≡C—, —CH=$CR^6$ or together with B can also mean a direct bond, their salts with physiologically compatible bases and their cyclodextrin clathrates.

8 Claims, No Drawings

NEW LEUKOTRIENE-B₄ DERIVATIVES, PROCESS FOR THEIR PRODUCTION AND THEIR USE AS PHARMACEUTICAL AGENTS

This application is a continuation, of application Ser. No. 07/961,728, filed Jan. 12, 1993, now abandoned.

LTB₄ antagonists, which contain a six-membered ring as a basic structural element, are already known from German laid-open specification DE 39 17 597.

The invention relates to new leukotriene-B₄ derivatives, the process for their production as well as their use as pharmaceutical agents.

Leukotriene B₄ (LTB₄) was discovered in 1979 by B. Samuelsson et al. as a metabolite of arachidonic acid. In the biosynthesis, leukotriene A₄ is formed by the enzyme 5-lipoxygenase first as a central intermediate product, which then is converted by a specific hydrolase to the LTB₄.

eral more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10, 277 (1987). It follows from the above that LTB₄ is an important inflammation mediator for inflammatory diseases, in which leukocytes invade the affected tissue.

It is known from the LTB₄ that it causes the adhesion of leukocytes on the blood vessel wall. LTB₄ is chemotactically effective, i.e., it triggers a directed migration of leukocytes in the direction of a gradient of increasing concentration. Further, because of its chemotactic activity, it indirectly changes the vascular permeability, and a synergism with prostaglandin E₂ is observed. LTB₄ obviously plays a decisive role in inflammatory, allergic and immunological processes.

Leukotrienes and especially LTB₄ are involved in

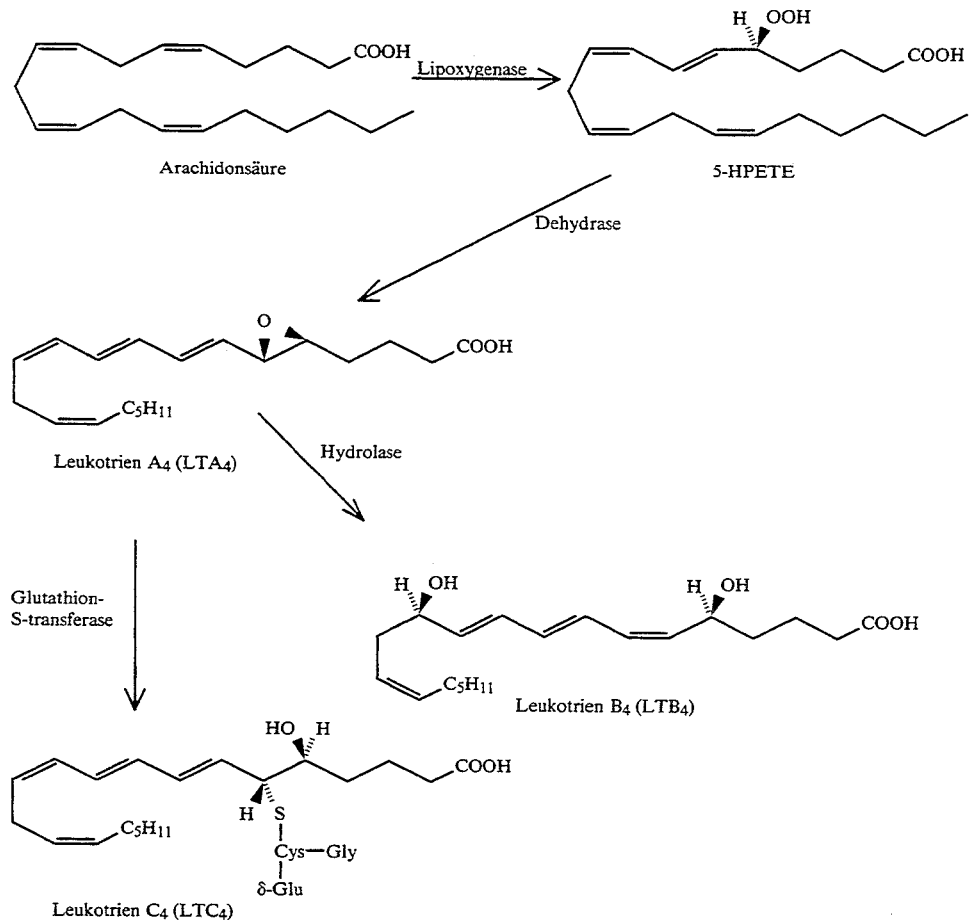

KEY:
Arachidonsäure = arachidonic acid
Leukotrien A₄ (LTA₄) = leukotriene A₄ (LTA₄)
Glutathion - S-transferase = glutathione - S-transferase
Leukotrien B₄ (LTB₄) = leukotriene B₄ (LTB₄)
Leukotrien C₄ (LTC₄) = leukotriene C₄ (LTC₄)

The nomenclature of the leukotrienes can be gathered from the following works:

a) B. Samuelsson et al., Prostaglandins 19, 645 (1980); 17, 785 (1979).

b) C. N. Serhan et al., Prostaglandins 34, 201 (1987).

The physiological and especially the pathophysiological importance of leukotriene B₄ is summarized in sevskin diseases, which accompany inflammatory processes (increased vessel permeability and formation of edemas, cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis.

Further, leukotrienes and $LTB_4$ are involved especially in arthritis, chronic lung disease (e.g., asthma), rhinitis and inflammatory intestinal diseases.

Antagonists against $LTB_4$ receptors or inhibitors of those enzymes which are involved in the synthesis of the $LTB_4$ should be effective as specific medications, especially against diseases which accompany inflammations and allergic reactions.

Besides the therapeutic possibilities, which can be derived from counteracting of $LTB_4$ action with $LTB_4$ analogs, the usefulness and potential use of leukotriene-$B_4$ agonists for the treatment of fungus diseases of the skin was also able to be shown (H. Katayama, Prostaglandins 34, 797 (1988)).

The invention relates to leukotriene-$B_4$ derivatives of formula I

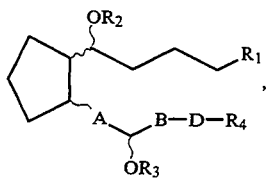

in which $R^1$ means $CH_2OH$, $CH_3$, $CF_3$, $COOR^5$, $CONR^6R^7$, or $R^1$ together with $R^2$ means a carbonyl group, $R^2$ and $R^3$ are the same or different and represent H or an organic acid radical with 1-15C atoms, $R^4$ symbolizes H, $C_1$-$C_{10}$ alkyl optionally substituted once or several times by chlorine or bromine, $C_3$-$C_{10}$ cycloalkyl, $C_6$-$C_{10}$ aryl radical optionally substituted, independent from one another, once or several times by chlorine, bromine, phenyl, $C_1$-$C_4$ alkyl, $C_1$-$C_4$ alkoxy, fluoromethyl, chloromethyl, trifluoromethyl, carboxy or hydroxy, or a 5-6-membered aromatic heterocyclic ring with at least 1 heteroatom, $R^5$ means hydrogen, $C_1$-$C_{10}$ alkyl, $C_3$-$C_{10}$ cycloalkyl, $C_6$-$C_{10}$ aryl radical optionally substituted by 1-3 chlorine, bromine, phenyl, $C_1$-$C_4$ alkyl, $C_1$-$C_4$ alkoxy, fluoromethyl, chloromethyl, trifluoromethyl, carboxy or hydroxy, $CH_2$—$CO$—($C_6$-$C_{10}$) aryl or a 5-6-membered ring with at least 1 heteroatom, A symbolizes a trans, trans-$CH=CH$—$CH=CH$, a —$CH_2CH_2$—$CH=CH$— or a tetramethylene group, B symbolizes a $C_1$-$C_{10}$ straight-chain or branched-chain alkylene group, which optionally can be substituted by fluorine or the group

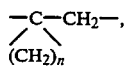

D can mean a direct bond, oxygen, sulfur, —$C\equiv C$—, —$CH=CR^8$ or together with B can also mean a direct bond, $R^6$ and $R^7$ are the same or different and represent H or $C_1$-$C_4$ alkyl or $R^7$ represents H and $R^6$ represents $C_1$-$C_{10}$ alkanoyl or $C_1$-$C_{10}$ alkanesulfonyl, $R^8$ means H, $C_1$-$C_5$ alkyl, chlorine, bromine, n is 3-5 as well as, if $R^5$ means hydrogen, its salts with physiologically compatible bases and its cyclodextrin clathrates.

Groups $OR^2$ and $OR^3$ can be in $\alpha$- or $\beta$-position. Formula I comprises both racemates and the possible pure diastereomers and enantiomers.

As alkyl groups $R^5$, straight-chain or branched-chain alkyl groups with 1-10C atoms are suitable, such as, for example, methyl, ethyl, propyl, butyl, isobutyl, tert-butyl, pentyl, neopentyl, hexyl, heptyl, decyl. Alkyl groups $R^5$ can optionally be substituted once to several times by halogen atoms, alkoxy groups, optionally substituted aryl or aroyl groups with 6-10C atoms (for substitution, see under Aryl $R^5$), dialkylamino and trialkylammonium with 1-4C atoms in the alkyl part, and the simple substitution is to be preferred. As substituents, there can be mentioned, for example, fluorine, chlorine or bromine, phenyl, dimethylamino, diethylamino, methoxy, ethoxy. As preferred alkyl groups $R^5$, those with 1-4C atoms are to be mentioned.

Cycloalkyl group $R^5$ can contain 3-10, preferably 5 and 6 carbon atoms in the ring. The rings can be substituted by alkyl groups with 1-4 carbon atoms. For example, there can be mentioned cyclopentyl, cyclohexyl, methylcyclohexyl.

As aryl groups $R^5$, both substituted and unsubstituted aryl groups with 6-10C atoms are suitable, such as, for example, phenyl, 1-naphthyl and 2-naphthyl, which respectively can be substituted by 1-3 halogen atoms (F, Cl, Br), a phenyl group, 1-3 alkyl groups with respectively 1-4C atoms, a chloromethyl, fluoromethyl, trifluoromethyl, carboxyl, hydroxy or alkoxy group with 1-4C atoms. Preferred substituents in 3- and 4-position on the phenyl ring are, for example, fluorine, chlorine, alkoxy or trifluoromethyl, however, hydroxy in 4-position.

As heterocyclic groups $R^5$, 5- and 6-membered aromatic heterocycles are suitable, which contain at least 1 heteroatom, preferably nitrogen, oxygen or sulfur. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, i.a.

As acid radical $R^6$, physiologically compatible acid radicals are suitable. Preferred acids are organic carboxylic acids and sulfonic acids with 1-15 carbon atoms, which belong to the aliphatic, cycloaliphatic, aromatic, aromatic-aliphatic and heterocyclic series. These acids can be saturated, unsaturated and/or polybasic and/or substituted in the usual way. As examples for the substituents, $C_{1-4}$ alkyl, hydroxy, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecanoic acid, lauric acid, tridecanoic acid, myristic acid, pentadecanoic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen (F, Cl, Br) or trifluoromethyl, hydroxy, $C_{1-4}$ alkoxy or carboxy groups, nicotinic acid, isonicotinic acid, furan-2-carboxylic acid, cyclopentylpropionic acid. As especially preferred acyl radicals and alkanesulfonyl radicals, those with up to 10 carbon atoms are suitable. As sulfonic acids, for example, methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis-(β-chloroethyl)aminosulfonic acid, N,N-diisobutylaminosulfonic acid, N,N-dibutylaminosulfonic acid, pyrrolidino, piperidino, piperazino, N-methylpiperazino, and morpholinosulfonic acid are suitable.

As alkyl groups $R^4$, straight-chain and branched-chain, saturated and unsaturated alkyl radicals, preferably saturated, with 1–14, especially 1–10C atoms, are suitable, which optionally can be substituted by optionally substituted phenyl (for substitution, see under Aryl $R^5$). For example, there can be mentioned methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups. If alkyl groups $R^4$ are halogen-substituted, fluorine, chlorine and bromine are suitable as halogens.

As examples for halogen-substituted alkyl groups $R^4$, alkyls with terminal trifluoromethyl groups are suitable.

Cycloalkyl group $R^4$ can contain 3–10, preferably 3–6 carbon atoms in the ring. The rings can be substituted by alkyl groups with 1–4 carbon atoms. For example, there can be mentioned cyclopropyl, cyclobutyl, cyclopentyl, cyclohexyl, methylcyclohexyl.

As substituted or unsubstituted aryl groups $R^4$, for example, phenyl, 1-naphthyl and 2-naphthyl, which respectively can be substituted by 1–3 halogen atoms, a phenyl group, 1–3 alkyl groups with respectively 1–4C atoms, a chloromethyl, fluoromethyl, trifluoromethyl, carboxyl, $C_1$-$C_4$ alkoxy or hydroxy group are suitable. The substitution in 3- and 4-position on the phenyl ring, for example, by fluorine, chlorine, alkoxy or trifluoromethyl or in 4-position by hydroxy is preferred.

As heterocyclic aromatic groups $R^4$, 5- and 6-membered heterocycles are suitable which contain at least 1 heteroatom, preferably nitrogen, oxygen or sulfur. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a.

As alkylene group B, straight-chain or branched-chain, saturated or unsaturated alkylene radicals, preferably saturated with 1–10, especially with 1–5C atoms are suitable, which optionally can be substituted by fluorine atoms. For example, there can be mentioned: methylene, fluoromethylene, difluoromethylene, ethylene, 1,2-propylene, ethyl ethylene, trimethylene, tetramethylene, pentamethylene, 1,2-difluoroethylene, 1-fluoroethylene, 1-methyltetramethylene, 1-methyltrimethylene, 1-methylene-ethylene, 1-methylenetetramethylene.

Alkylene group B can further represent the group

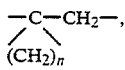

in which n=3–5, preferably 4–5.

As acid radicals $R^2$ and $R^3$, physiologically compatible acid radicals are suitable. Preferred acids are organic carboxylic acids and sulfonic acids with 1–15 carbon atoms, which belong to the aliphatic, cyclo-aliphatic, aromatic, aromatic-aliphatic or heterocyclic series. These acids can be saturated, unsaturated and/or polybasic and/or substituted in the usual way. As examples for the substituents, $C_{1-4}$ alkyl, hydroxy, $C_{1-4}$ alkoxy, oxo or amino groups or halogen atoms (F, Cl, Br) can be mentioned.

For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecanoic acid, lauric acid, tridecanoic acid, myristic acid, pentadecanoic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen (F, Cl, Br), trifluoromethyl, hydroxy, $C_{1-4}$ alkoxy or carboxy groups, nicotinic acid, isonicotinic acid, furan-2-carboxylic acid, cyclopentylpropionic acid. As especially preferred acid radicals $R^2$ and $R^3$, acyl radicals with up to 10 carbon atoms are suitable.

Alkyl radicals $R^6$ and $R^7$ are straight-chain or branched alkyl radicals, especially straight-chain, such as, for example, methyl, ethyl, propyl, butyl, pentyl, hexyl, especially preferably methyl.

$R^8$ as $C_{1-5}$ alkyl means straight-chain or branched-chain alkyl radicals such as were already mentioned for $R^4$ or $R^5$. Preferred alkyl radicals $R^8$ are methyl, ethyl, propyl and isopropyl.

Inorganic and organic bases are suitable for salt formation, as they are known to one skilled in the art for forming physiologically compatible salts. For example, there can be mentioned alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

Preferred compounds of this invention are compounds of formula I, in which the radicals have the following meaning:

$R^1$ is $CH_2OH$, $COOR^5$ with $R^5$ meaning a hydrogen atom, an alkyl radical with 1–10C atoms, a cycloalkyl radical with 5–6C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, A is a trans, trans-CH=CH—CH=CH— or tetramethylene group;

B is a straight-chain or branched-chain, saturated or unsaturated alkylene group with up to 10C atoms, which optionally can be substituted by fluorine or the group

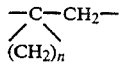

with n=3–5;

D is a direct bond, oxygen, sulfur, a —C≡C— group or a —CH=CR$^8$— group with $R^8$ as hydrogen, $C_{1-5}$ alkyl, chlorine or bromine;

B and D together are a direct bond;

$R^2$ and $R^3$ are the same or different and mean hydrogen or an organic acid radical with 1-15C atoms;

$R^1$ and $R^2$ together are a carbonyl group;

$R^4$ is a hydrogen atom, $C_{1-10}$ alkyl, cycloalkyl with 5-6C atoms, a phenyl radical optionally substituted by 1-2 chlorine, bromine, phenyl, $C_{1-4}$ alkyl, $C_{1-4}$ alkoxy, chloromethyl, fluoromethyl, trifluoromethyl, carboxy or hydroxy and if $R^5$ means a hydrogen atom, their salts with physiologically compatible bases and their cyclodextrin clathrates.

Especially preferred compounds of this invention are compounds of formula I, in which the radicals have the following meaning:

$R^1$ is $CH_2OH$, $COOR^5$ with $R^5$ meaning a hydrogen atom, an alkyl radical with 1-4C atoms;

A is a trans, trans-CH=CH-CH=CH— or tetramethylene group;

B is a straight-chain or branched-chain alkylene group with up to 5C atoms;

D is a direct bond or a —C≡C— group or a —CH=CR$^8$ group with $R^8$ as hydrogen or $C_{1-5}$ alkyl;

B and D together are a direct bond;

$R^2$ and $R^3$ are the same or different and mean hydrogen or an organic acid radical with 1-6C atoms;

$R^1$ and $R^2$ together are a carbonyl group;

$R^4$ is a hydrogen atom or $C_{1-10}$ alkyl and if $R^5$ means a hydrogen atom, their salts with physiologically compatible bases and their cyclodextrin clathrates.

The invention further relates to a process for the production of compounds of formula I according to the invention, which is characterized in that an aldehyde of formula II

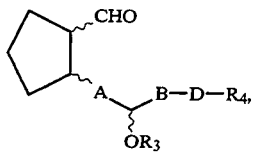

(II)

in which A, B, D, $R^3$ and $R^4$ have the above-indicated meanings, optionally after protection of free hydroxy groups with a magnesium-organic compound of formula III, $$X-Mg-CH_2-CH_2-CH_2-CH_2-R^9 \quad (III),$$

in which X represents chlorine, bromine or iodine and $R^9$ represents —$CH_3$, $CF_3$ or —$OR^{10}$, in which $R^{10}$ means an easily cleavable ether radical, is reacted and optionally then isomers are separated in any sequence, protected hydroxy groups are released and/or a free hydroxy group is esterified and/or the 1-hydroxy group is oxidized to carboxylic acid and/or double bonds are hydrogenated and/or an esterified carboxyl group ($R^1$=$COOR^5$) is saponified and/or reduced and/or a carboxyl group ($R^5$=H) is esterified and/or a free carboxy group ($R^5$=H) is converted to an amide ($R^1$=$CONHR^6R^7$) or a carboxyl group with a physiologically compatible base is converted to a salt.

As ether radicals $R^9$ in the compound of formula III, the radicals familiar to one skilled in the art are suitable. Easily cleavable ether radicals, such as, for example, dimethyl-tert-butylsilyl, trimethylsilyl, tribenzylsilyl, diphenyl-tert-butylsilyl, tetrahydropyranyl, tetrahydrofuranyl and α-ethoxyethyl, to name only a few, are preferable.

The reaction of the compound of formula II with an organometallic compound of formula III takes place in a way known in the art in an inert solvent or solvent mixture, such as, for example, diethyl ether, tetrahydrofuran, dioxane, toluene, dimethoxyethane, preferably diethyl ether or tetrahydrofuran. The reaction is performed at temperatures between −100° C. and 60° C., preferably at −78° C. to 0° C.

The production of the compound of formula III necessary for this reaction takes place by reaction of the corresponding hydroxy halide by etherification with dihydropyran and p-toluenesulfonic acid and subsequent reaction with magnesium.

The reduction to the compounds of formula I with $R^1$ meaning a $CH_2OH$ group is performed with a reducing agent suitable for the reduction of esters or carboxylic acids, such as, for example, lithium aluminum hydride, diisobutyl aluminum hydride, etc. As solvent, diethyl ether, tetrahydrofuran, dimethoxyethane, toluene, etc., are suitable. The reduction is performed at temperatures of −30° C. up to boiling temperature of the solvent used, preferably 0° C. to 30° C.

The esterification of the alcohols of formula I ($R^2$=H and/or $R^3$=H) takes place in a way known in the art. For example, the esterification takes place in that an acid derivative, preferably an acid halide or acid anhydride, is reacted in the presence of a base, such as, for example, NaH, pyridine, triethylamine, tributylamine or 4-dimethylaminopryidine with an alcohol of formula I. The reaction can be performed without solvent or in an inert solvent, preferably acetone, acetonitrile, dimethylacetamide, DMSO at temperatures above or below room temperature, for example, between −80° C. to 100° C., preferably at room temperature.

The oxidation of the 1-hydroxy group is performed according to the methods known to one skilled in the art. As oxidizing agents, for example, there can be used: pyridinium dichromate (Tetrahedron Letters, 1979, 399), Jones reagent (J. Chem. Soc. 1953, 2555) or platinum/oxygen (Adv. in Carbohydrate Chem. 17, 169 (1962)) or Collins oxidation and subsequent Jones oxidation. The oxidation with pyridinium dichromate is performed at temperatures of 0° C. to 100° C., preferably 20° C. to 40° C. in a solvent inert toward the oxidizing agent, for example, dimethylformamide.

The oxidation with Jones reagent is performed at temperatures of −40° C. to +40° C., preferably 0° C. to 30° C. in acetone as solvent.

The oxidation with platinum/oxygen is performed at temperatures of 0° C. to 60° C., preferably 20° C. to 40° C. in a solvent inert toward the oxidizing agent, such as, e.g., ethyl acetate.

The saponification of the esters of formula I is performed according to the methods known to one skilled in the art, such as, for example, with basic catalysts. The compounds of formula I can be separated by the usual separating methods into the optical isomers.

The release of the functionally modified hydroxy groups takes place according to known methods. For example, the cleavage of hydroxy protecting groups, such as, for example, the tetrahydropyranyl radical, is performed in an aqueous solution of an organic acid, such as, e.g., oxalic acid, acetic acid, propionic acid, i.a., or in an aqueous solution of an inorganic acid, such as, e.g., hydrochloric acid. To improve the solubility, a water-miscible, inert organic solvent is suitably added.

Suitable organic solvents are, e.g., alcohols, such as methanol and ethanol, and ethers, such as dimethoxyethane, dioxane and tetrahydrofuran. Tetrahydrofuran is preferably used. The cleavage is performed preferably at temperatures between 20° C. and 80° C. The cleavage of the silyl ether protecting groups takes place, for example, with tetrabutylammonium fluoride or with potassium fluoride in the presence of a crown ether. As solvent, for example, tetrahydrofuran, diethyl ether, dioxane, methylene chloride, etc., are suitable. The cleavage is performed preferably at temperatures between 0° C. and 80° C.

The saponification of the acyl groups takes place, for example, with alkali or alkaline-earth carbonates or hydroxides in an alcohol or in the aqueous solution of an alcohol. As an alcohol, aliphatic alcohols are suitable, such as, e.g., methanol, ethanol, butanol, etc., preferably methanol. As alkali carbonates and hydroxides, potassium salts and sodium salts can be mentioned. The potassium salts are preferred.

As alkaline-earth carbonates and hydroxides, for example, calcium carbonate, calcium hydroxide and barium carbonate are suitable. The reaction takes place at −10° C. to +70° C., preferably at +25° C.

The introduction of ester group

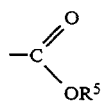

for $R^1$, in which $R^5$ represents an alkyl group with 1–10C atoms, takes place according to the methods known to one skilled in the art. The 1-carboxy compounds are reacted, for example, with diazohydrocarbons in a way known in the art. The esterification with diazohydrocarbons takes place, e.g., in that a solution of the diazohydrocarbon in an inert solvent, preferably in diethyl ether, is mixed with the 1-carboxy compound in the same or in another inert solvent, such as, e.g., methylene chloride. After completion of the reaction in 1 to 30 minutes, the solvent is removed and the ester is purified in the usual way. Diazoalkanes are either known or can be produced according to known methods [Org. Reactions Vol. 8, pages 389–394 (1954)].

The introduction of ester group

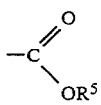

for $R^1$, in which $R^5$ represents a substituted or unsubstituted aryl group, takes place according to the methods known to one skilled in the art. For example, the 1-carboxy compounds with the corresponding arylhydroxy compounds are reacted with dicyclohexylcarbodiimide in the presence of a suitable base, for example, pyridine, DMAP, triethylamine, in an inert solvent. As solvent, methylene chloride, ethylene chloride, chloroform, ethyl acetate, tetrahydrofuran, preferably chloroform, are suitable. The reaction is performed at temperatures between −30° C. and +50° C., preferably at 10° C.

If C=C double bonds contained in the primary product are to be reduced, the hydrogenation takes place according to methods known in the art.

The hydrogenation of the $\Delta^{8,10}$ diene system is performed in a way known in the art at low temperatures, preferably at about −20° C. to +30° C. in a hydrogen atmosphere in the presence of a noble metal catalyst. As catalyst, for example, 10% palladium on carbon is suitable.

The leukotriene-$B_4$ derivatives of formula I with $R^5$ meaning a hydrogen atom can be converted to a salt with suitable amounts of the corresponding inorganic bases with neutralization. For example, during dissolving of the corresponding acids in water, which contains the stoichiometric amount of the base, the solid inorganic salt is obtained after evaporation of the water or after addition of a water-miscible solvent, e.g., alcohol or acetone.

For the production of an amine salt, the $LTB_4$ acid, e.g., is dissolved in a suitable solvent, for example, ethanol, acetone, diethyl ether, acetonitrile or benzene and at least the stoichiometric amount of the amine is added to this solution. In this way, the salt usually accumulates in solid form or is isolated after evaporation of the solvent in the usual way.

The introduction of amide group

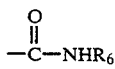

with $R_6$ meaning alkanoyl takes place according to the methods known to one skilled in the art. The carboxylic acids of formula I ($R_5$=H) are first converted to the mixed anhydride in the presence of a tertiary amine, such as, for example, triethylamine, with chloroformic acid isobutyl ester. The reaction of the mixed anhydride with the alkali salt of the corresponding amide or with ammonia ($R_6$=H) takes place in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C.

Another possibility for the introduction of amide group

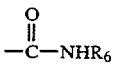

consists in the reaction of a 1-carboxylic acid of formula I ($R_5$=H), in which free hydroxy groups are optionally intermediately protected, with compounds of formula IV,

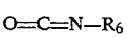

$$O=C=N-R_6 \qquad (IV),$$

in which $R_6$ has the above-indicated meaning.

The reaction of the compound of formula I ($R_5$=H) with an isocyanate of formula IV takes place optionally by adding a tertiary amine, such as, e.g., triethylamine or pyridine. The reaction can be performed without solvent or in an inert solvent, preferably acetonitrile, tetrahydrofuran, acetone, dimethylacetamide, methylene chloride, diethyl ether, toluene, at temperatures between −80° C. to 100° C., preferably at 0° C. to 30° C.

For production of the other amides, for example, the desired acid anhydrides can be reacted with ammonia or the corresponding amines.

If the initial product contains OH groups in the leukotriene-$B_4$ radical, these OH groups are also reacted. If finally end products are desired which contain free hydroxyl groups, a start is suitably made from initial products in which the latter are intermediately protected by preferably easily cleavable ether or acyl radicals.

The separation of enantiomers and/or diastereomers takes place according to the methods known to one skilled in the art, for example, high-pressure liquid chromatography on optically active vehicles.

The compounds of formula II being used as initial material can be produced, for example, by cis- or trans-bis-1,2-hydroxymethyl-cyclopentane (obtainable by reduction from cis- or trans-cyclopentane-1,2-dicarboxylic acid, see, e.g., A. Padwa et al., J. Org. Chem. 54, 817 (1989); O. Caamaus et al., Eur. J. Med. Chem. 22, 311 (1987)) being converted in a way known in the art to the monosilylether of formula V

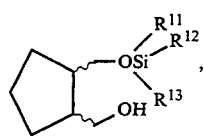  (V)

in which $R^{11}$, $R^{12}$ and $R^{15}$ are the same or different and mean $C_1$-$C_4$ alkyl or phenyl.

By oxidation, e.g., with Collins reagent or by the Swern process, there is obtained the aldehyde of formula VI

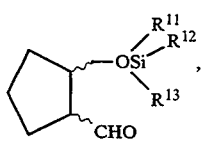  (VI)

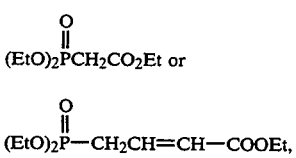

(EtO)$_2$PCH$_2$CO$_2$Et or  (VII)

(EtO)$_2$P—CH$_2$CH=CH—COOEt,  (VIII)

which is converted in a Wittig-Horner olefination with the phosphonate of formula VII and a base and optionally subsequent hydrogenation as well as subsequent reduction of the ester group, oxidation of the primary alcohol, repeated Wittig-Horner olefination with the phosphonate of formula VII and optionally subsequent hydrogenation to the ester of formula IX or in a Wittig-Horner reaction of the aldehyde of formula VI with a phosphate of formula VIII, in which A

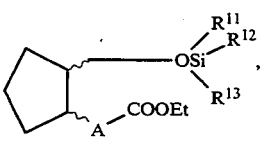  (IX)

has the above-indicated meaning. As bases, for example, potassium-tert-butylate, diazabicyclononane or sodium hydride are suitable. Reduction of the ester group, for example with DIBAH and subsequent oxidation of the obtained primary alcohol, e.g., with manganese dioxide or Collins reagent results in the aldehyde of formula X

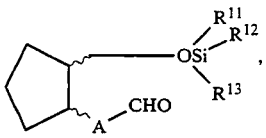  (X)

The organometallic reaction of the aldehyde of formula X with a Grignard reagent of formula XI,

X—MG—B—D—R$_4$  (XI), in which B, D and $R^4$ exhibit the above-indicated meanings and X means chlorine, bromine or iodine, results, after protection of the hydroxy group and optionally diastereomer separation (for example, by acylation) in the compounds of formula XII

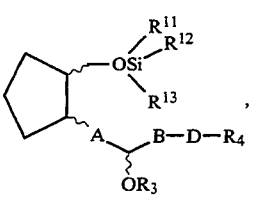  (XII)

The production of the compound of formula XI necessary for the organometallic reaction takes place by reaction of the corresponding terminal halide with magnesium. By reaction of silylether XII with tetrabutylammonium fluoride, the alcohol of formula XIII is obtained.

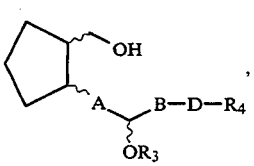  (XIII)

The oxidation of the primary alcohol group in XIII, e.g., Collins reagent or pyridinium dichromate, results in the aldehyde of formula II.

The compounds of formula XII, in which B means a CH$_2$ group and D means a —ClC— or CH=CR$^8$ group, can be attained, for example, by an organometallic reaction of a propargyl halide and subsequent alkylation with a corresponding alkyl halide and optionally subsequent Lindlar hydrogenation.

An alternative design of the lower chain starts from the aldehyde of formula XIV, which resulted from the Wittig-Horner reaction of aldehyde VI and subsequent reduction and oxidation.

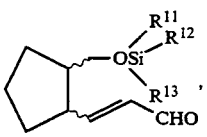  (XIV)

Wittig-Horner olefination of aldehyde XIII with a phosphonate of formula XV

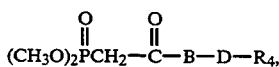  (XV)

and reduction of the resulting ketone then resulted in the alcohol of formula XIII.

The incorporation of the chemically and metabolically labile cis-$\Delta^{6,7}$ double bond of the $LTB_4$ in a cis- or trans-1,2-substituted cyclopentyl ring results in a stabilization, and especially by further derivatizing of the functional groups, $LTB_4$ derivatives are obtained which can act as $LTB_4$ antagonists.

The compounds of formula I act in an antiinflammatory and antiallergic manner. In addition, they have antimycotic properties. Consequently, the new leukotriene-$B_4$ derivatives of formula I represent valuable pharmaceutical active ingredients. The compounds of formula I are especially suitable for topical administration, since they exhibit a dissociation between desired topical effectiveness and undesirable systemic side effects.

The new leukotriene-$B_4$ derivatives of formula I are suitable in combination with the auxiliary agents and vehicles usual in galenic pharmaceutics for topical treatment of contact dermatitis, eczemas of the most varied types, neurodermatoses, erythrodermia, pruritus vulvae et ani, rosacea, lupus erythematosus cutaneus, psoriasis, lichen ruber planus et verrucosis and similar skin diseases.

The production of the pharmaceutical agent specialties takes place in the usual way by the active ingredients being converted with suitable additives to the desired form of administration, such as, for example: solutions, lotions, ointments, creams or plasters.

In the thus formulated pharmaceutical agents, the active ingredient concentration depends on the form of administration. In lotions and ointments, an active ingredient concentration of 0.0001% to 1% is preferably used.

Further, the new compounds optionally in combination with the usual auxiliary agents and vehicles are also well-suited for the production of inhalants, which can be used to treat allergic diseases of the respiratory system, such as, for example, bronchial asthma or rhinitis.

Further, the new leukotriene-$B_4$ derivatives are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat allergic diseases of the intestinal tract, such as colitis ulcerosa and colitis granulomatosa.

The new leukotriene-$B_4$ derivatives can also be used in combination, such as, e.g., with lipoxygenase inhibitors, cyclooxygenase inhibitors, prostacyclin agonists, thromboxane antagonists, leukotriene-$D_4$ antagonists, leukotriene-$E_4$ antagonists, leukotriene-$F_4$ antagonists, phosphodiesterase inhibitors, calcium antagonists or PAF antagonists.

The following embodiments are used to explain the process according to the invention in more detail. In the examples, diastereoisomers in 12-position not characterized in more detail were characterized as polar or nonpolar (e.g., diastereomer nonpolar (12)).

EXAMPLES

Example 1

(+/−)-(5RS)-5-Acetoxy-5-[cis-(2RS)-2-((1E,3E)-(5RS)-5-acetoxy-1,3-tridecadienyl)(1RS)-cyclopentyl]-pentanoic acid diastereomer nonpolar (12)

A solution of 11.1 g of 4-chloro-1-(tert-butyldimethylsilyloxy)-butane in 10 ml of tetrahydrofuran is instilled in 2.44 g of magnesium at 25° C. under argon, a crystal of iodine is added, it is heated for 10 minutes to 70° C., stirred for 30 minutes at 25° C. and diluted with 31 ml of tetrahydrofuran.

A solution of 495 mg of cis-(1RS)-1-formyl-(2RS)-2[(1E,3E)-(5RS)-5-acetoxy-1,3-tridecadienyl]-cyclopentane (diastereomer nonpolar (12)) in 1.7 ml of tetrahydrofuran is instilled in 2.96 ml of the above magnesium-organic solution at −70° C. under argon and stirred for 1.5 hours at −70° C. It is mixed with 8 ml of saturated ammonium chloride solution, extracted three times with ether, the organic phase is shaken with brine, dried on sodium sulfate and concentrated by evaporation in a vacuum. The residue is chromatographed on silica gel. With hexane/ether (8+2), 480 mg of the alcohol is obtained as colorless oil.

IR($CHCl_3$): 3600, 2930, 2860, 1725, 1373, 1450, 993, 836 $cm^{-1}$.

For acetylation, 2.0 ml of acetic anhydride is added to a solution of 1.8 g of the above-described alcohol in 5 ml of pyridine and stirred for 23 hours at room temperature. Then it is concentrated by evaporation in a vacuum while adding toluene and the residue is chromatographed on silica gel. With hexane/ether (8+2), 1.88 g of the acetate is obtained as colorless oil.

IR: 2930, 2862, 1730, 1610, 1375, 1255, 993, 840 $cm^{-1}$.

For silylether cleavage, 1.35 g of the above-produced acetate in 80 ml of tetrahydrofuran is stirred with 2.26 g of tetrabutylammonium fluoride for 20 minutes at 0° C. and for 4 hours at 24° C. under argon. Then, it is diluted with ether, washed three times with water, dried on magnesium sulfate and concentrated by evaporation in a vacuum. The residue is chromatographed with ether on silica gel. In this way, 960 mg of the 1-alcohol is obtained as colorless oil.

IR: 3600 (broad), 2930, 2860, 1736, 1610, 1373, 1250, 990 $cm^{-1}$.

For oxidation of the 1-hydroxy group, 5.4 g of Collins reagent is added to 940 mg of the above-produced alcohol in 54 ml of methylene chloride at 0° C. and stirred for 20 minutes at 0° C. Then, it is diluted with a mixture of hexane/ether (1+1), Celite is added, filtered, washed with hexane/ether (1+1) and concentrated by evaporation in a vacuum. The thus obtained 1-aldehyde is immediately used without further purification.

1.67 ml of Jones reagent (J. Chem. Soc. 1953, 2555) is instilled in a solution of 800 mg of the above-produced aldehyde in 29 ml of acetone with stirring at −25° C. and stirred for 15 minutes at −25° C. under argon. Then, 5.8 ml of isopropanol is added, stirred for 5 minutes, diluted with 200 ml of ether, shaken twice with brine, dried on magnesium sulfate and concentrated by evaporation in a vacuum. The residue is chromatographed on silica gel. With hexane/ether (1+1), 570 ml of the title compound is obtained as colorless oil.

IR: 3520 (broad), 2930, 2860, 1726, 1373, 1255, 990, 948 $cm^{-1}$.

The initial material for the above title compound is produced as follows:

1a) 3-[cis-1-(tert-Butyl-dimethylsilyloxymethyl)-cyclopentl-2-yl]-(2E)-propenoic acid ethyl ester 127 ml of a 1.2 molar solution of diisobutylaluminum hydride in toluene is instilled in a solution of 8.7 g of 2-hydroxymethyl-cyclopentanecarboxylic acid lactone (O. Caamano et al., Euro. J. Med. Chem. 22, 311 (1987)) in 127 ml of toluene at 0° C. under argon and stirred for 50 minutes at 0° C. Then, 25 ml of isopropanol and 63 ml of water are instilled, stirred for 2 hours at 22° C., filtered washed with methylene chloride and concentrated by evaporation in a vacuum. The residue is purified by chromatography on silica gel. With ethyl acetate/hexane (4+1), 7 g of cis-1,2-dihydroxymethyl-cyclopentane is obtained as colorless liquid.

IR: 3600, 3400, 2960, 1060 cm$^{-1}$.

A solution of 13 g of the above-produced diol in 5 ml of tetrahydrofuran is instilled in a suspension of 4.36 g of sodium hydride (as a 55% suspension in mineral oil) in 200 ml of tetrahydrofuran at 22° C. and stirred for 45 minutes at 22° C. Then, 15 g of tert-butyldimethylsilyl chloride is madded, stirred for 45 minutes at 22° C. and then diluted with about 1.5 liters of ether. The ether extract is washed with 10% potassium carbonate solution, shaken three times with water, dried with sodium sulfate and concentrated by evaporation in a vacuum. The residue is chromatographed on silica gel. With hexane/ether (95+5), 20.9 cis-1-(tert-butyl-dimethylsilyloxymethyl)-2-hydroxymethylcyclopentane is obtained as colorless liquid.

IR: 3420 (broad), 2960, 2863, 1260, 840 cm$^{-1}$.

84 g of Collins reagent (chromic acid-pyridine complex) is added to a solution of 16.9 g of the above-described monosilylether in 835 ml of methylene chloride at 0° C. and stirred for 30 minutes at 0° C. Then, it is diluted with a mixture of hexane/ether (3+2), Celite is added, filtered and concentrated by evaporation in a vacuum. 16.2 g of the aldehyde is obtained which is used without further purification.

IR: 2958, 2930, 2860, 2740, 1713, 840 cm$^{-1}$.

For Wittig olefination, 20.7 g of phosphonoacetic acid triethyl ester and 12.6 g of diazabicycloundecene (DBU) are added at 24° C. to a stirred suspension of 3.9 g of lithium chloride in 277 ml of acetonitrile and stirred for 15 minutes. Then, a solution of 16 g of the above-described aldehyde in 43 ml of acetonitrile is instilled, stirred for 2.5 hours at 24° C. and then diluted with ether. It is shaken in succession with water, 10% sulfuric acid and water, dried with sodium sulfate and concentrated by evaporation in a vacuum. The residue is chromatographed with hexane/ether (95+5) on silica gel. In this way, 22.5 g of the title compound is obtained as colorless oil.

IR: 2960, 2860, 1710, 1650, 1260, 985, 840 cm$^{-1}$.

1b) 5-[cis-1-(tert-butyl-dimethylsilyloxymethyl)-cyclo-pent-2-yl]-(2E,4E)pentadienoic acid ethyl ester 120 ml of a 1.2 molar solution of diisobutylaluminum hydride in toluene is instilled in a solution of 22.5 g of the α,β-unsaturated ester, produced according to example 1a, in 500 ml of toluene at −70° C. under argon and stirred for 30 minutes at −70° C. Then, 30 ml of isopropanol and then 60 ml of water are instilled, stirred for 2 hours at 22° C., filtered, washed with methylene chloride and concentrated by evaporation in a vacuum. 22.5 g of the allyl alcohol is obtained, which is used without further purification.

IR: 3600, 3400, 2958, 840 cm$^{-1}$.

A solution of 20.35 g of the above-produced alcohol in 654 ml of toluene is mixed with 80 g of manganese dioxide and stirred for 5 hours at 24° C. Then, it is filtered, concentrated by evaporation and chromatographed on silica gel. With hexane/ether (92+8), 17.6 g of the aldehyde is eluted as colorless oil.

IR: 2960, 2860, 2745, 1730, 1633, 1470, 975, 840 cm$^{-1}$.

For Wittig olefination, 20.5 g of phosphonoacetic acid triethyl ester and 12.4 g of diazabicycloundecene are added at 24° C. to a stirred suspension of 3.88 g of lithium chloride in 274 ml of acetonitrile and stirred for 15 minutes. Then, a solution of 17.5 g of the above-described α,β-unsaturated aldehyde in 43 ml of acetonitrile is instilled, stirred for 4 hours at 24° C. and then diluted with ether. It is shaken in succession with water, 10% citric acid solution and water, dried with sodium sulfate and concentrated by evaporation in a vacuum. The residue is chromatographed with hexane/ether (9+1) on silica gel. In this way, 15.7 g of the title compound is obtained as colorless oil.

IR: 2958, 2860, 1705, 1640, 1616, 1255, 1003, 970, 838 cm$^{-1}$.

1c) 5-[cis-1-(tert-Butyl-dimethylsilyloxy-methyl-cyclo-pent-2-yl]-pentadien-1-ol 81 ml of a 1.2 molar solution of diisobutylaluminum hydride in toluene is instilled in a solution of 15 g of the ester, produced according to example 1b, in 416 ml of toluene at −70° C. under argon and stirred for 30 minutes at −70° C. Then, 15 ml of isopropanol and then 40 ml of water are instilled, stirred for 3 hours at 23° C., filtered, washed with methylene chloride and concentrated by evaporation in a vacuum. The residue is purified by chromatography on silica gel. With hexane/ether (8+2), 9.3 g of the alcohol is obtained as colorless oil.

IR: 3620, 3460, 838 cm$^{-1}$.

A solution of 9.3 g of the above-produced alcohol in 273 ml of toluene is mixed with 27.3 g of manganese dioxide and stirred for 6 hours at 24° C. Then, it is filtered, concentrated by evaporation and chromatographed on silica gel. With hexane/ether (9+1), 6.9 g of the title compound is obtained as colorless oil.

IR: 2955, 2858, 2740, 1678, 1632, 986, 838 cm$^{-1}$.

1d) (5RS)-5-Acetoxy-1-[cis-1-(tert-butyl-dimethylsilyloxymethyl)-cyclopent)-2-yl]-(1E,3E)-tridecadiene A solution of 17.8 g of octyl bromide in 24 ml of ether is instilled in 2.24 g of magnesium in 12 ml of ether with heating and stirred for 30 minutes at 25° C. A solution of 6.7 g of the aldehyde, produced according to example 1c, in 100 ml of ether is instilled in 17.2 ml (31.7 mmol) of this Grignard solution at −20° C. under argon and stirred for 45 minutes at −20° C. It is mixed with saturated ammonium chloride solution, extracted three times with ether, the organic phase is shaken with brine, dried on sodium sulfate and concentrated by evaporation in a vacuum. The residue is chromatographed on silica gel. With hexane/ethyl acetate mixtures, 3.35 of nonpolar diastereomeric alcohol and 3.6 g of the polar diastereomeric alcohol are obtained as colorless oils.

For acetylation, 3.1 ml of acetic anhydride is added to a solution of 3.35 g of the above-produced nonpolar diastereomeric alcohol in 8 ml of pyridine and stirred for 24 hours at room temperature.

Then, it is concentrated by evaporation in a vacuum while adding toluene and the residue is chromatographed on silica gel. With hexane/ether (95+5), 3.5 g of the title compound (nonpolar diastereomer) is obtained as colorless oil.

IR: 2938, 2860, 1725, 1655, 1252, 990, 838 cm$^{-1}$.

Analogously, 3.7 g of the title compound (as polar diastereomer) is produced from 3.6 g of the above-produced polar diastereomeric alcohol with 3.3 ml of acetic anhydride and 8.6 ml of pyridine.

IR: 2915, 2860, 1725, 1655, 1252, 990, 838 cm$^{-1}$.

1e) cis-(1RS)-1-Formyl-(2RS)-2-[(1E,3E)-(5RS)-5-acetoxy-1,3-tridecadienyl]cyclopentane Diastereomer nonpolar (12)

7.35 g of tetrabutylammonium fluoride is added to a solution of 3.5 g of the acetate (nonpolar diastereomer), produced according to example 1d, in 350 ml of tetrahydrofuran at 0° C., stirred for 15 minutes at 0° C. and for 5.5 hours at 24° C. Then, it is diluted with 1 liter of ether and washed three times with brine. It is dried on magnesium sulfate, concentrated by evaporation in a vacuum and the residue is chromatographed on silica gel. With hexane/ether (7+3), 2.45 g of the alcohol is eluted as colorless oil.

IR: 3620, 3450, 2930, 2860, 1725, 1260, 992 cm$^{-1}$.

18.4 g of Collins reagent (chromic acid-pyridine complex) is added to a solution of 2.4 g of the above-produced alcohol in 75 ml of methylene chloride at 0° C. and stirred for 20 minutes at 0° C. Then, it is diluted with a mixture of hexane/ether (1+1), Celite is added, filtered and concentrated by evaporation in a vacuum. The thus obtained aldehyde was used without further purification.

IR: 2930, 2860, 2730, 1721, 1250, 990 cm$^{-1}$.

Example 2

(+/−)-(5RS)-5-Hydroxy-5-[cis-(2RS)-2-((1E,3E)-(5RS)-5-hydroxy-1,3-tridecadienyl)-(1RS)-cyclopentyl]-pentanoic acid Diastereomer nonpolar (12)

7.7 ml of a 0.5 n aqueous lithium hydroxide solution is added to a solution of 360 mg of the diacetate, produced according to example 1, in 7.7 ml of methanol and stirred for 25 hours at 50° C. Then, it is acidified with a 10% sulfuric acid to pH 5, diluted with ethyl acetate, shaken three times with brine, dried with sodium sulfate and concentrated by evaporation in a vacuum. The residue is chromatographed with ether/ethanol (99+1) on silica gel. In this way, 197 mg of the title compound is obtained as colorless crystals (melting point 71° C.).

IR: 3400, 2928, 2850, 1725, 1360, 1230, 995, 930 cm$^{-1}$.

Example 3

(+/−)-(5RS)-5-Acetoxy-5-[cis-(2RS)-2-((1E,3E)-(5RS)-5-hydroxy-1,3-(tridecadienyl)-(1RS)-cyclopentyl]-pentanoic acid Diastereomer nonpolar (12)

5.5 ml of a 0.5 n sodium hydroxide solution is added to a solution of 255 mg of the nonpolar diastereomeric diacetate, produced according to example 1, in 5.5 ml of methanol at 23° C. and stirred for 1.5 hours at 23° C. under argon. Then, it is diluted with water and acidified at ice bath temperature with 10% sulfuric acid to pH 5. It is extracted with ethyl acetate, washed twice with brine, dried with sodium sulfate and concentrated by evaporation in a vacuum. The residue is chromatographed on silica gel. With ether/hexane (8+2), 202 mg of the title compound is obtained as colorless oil.

IR: 3420, 2922, 2850, 1727, 1710, 1700, 1272, 990, 960 cm$^{-1}$.

Example 4

(+/−)-(5RS)-5-Hydroxy-5-[cis-(2RS)-2-((1E,3E)-(5RS)-5-hydroxy-1,3-tridecadienyl)-(1RS)-cyclopentyl]-pentan-1-ol Diastereomer nonpolar (12)

180 mg of the nonpolar diastereomeric diacetate described in example 1 is stirred for 60 hours at 24° C. with 5.5 ml of a solution of potassium hydroxide in water and ethanol (production: 5 g of potassium hydroxide is dissolved in 67.5 ml of water and 182.5 ml of ethanol). Then, it is acidified with 10% citric acid solution to pH 6, extracted four times with 20 ml of methylene chloride each, the organic phase is shaken with brine, dried on magnesium sulfate and concentrated by evaporation in a vacuum. The residue is chromatographed with ethyl acetate on silica gel. In this way, 103 mg of the title compound is obtained as colorless oil.

IR: 3610, 3370 (broad), 2930, 2860, 993 cm$^{-1}$.

Example 5

(+/−)-(5RS)-5-Acetoxy-5-[cis-(2RS)-2-((1E,3E)-(5RS)-5-acetoxy-1,3-tridecadienyl)-(1RS)-cyclopentyl]-pentanoic acid Diastereomer polar (12)

A solution of 11.1 g of 4-chloro-1-(tert-butyldimethylsilyloxy)-butane in 10 ml of tetrahydrofuran is instilled in 2.44 g of magnesium at 25° C. under argon, a crystal of iodine is added, heated for 10 minutes to 75° C., stirred for 40 minutes at 25° C. and diluted with 31 ml of tetrahydrofuran.

A solution of 1.6 g of cis-(1RS)-1-formyl-(2RS)-2-[(1E,3E)-(5RS)-5-acetoxy-1,3-tridecadienyl]-(cyclopentane (diastereomer polar (12)) in 5.5 ml of tetrahydrofuran is instilled in 9.6 ml of the above magnesium-organic solution at −70° C. under argon and stirred for 1 hour at −70° C.

It is mixed with 30 ml of saturated ammonium chloride solution, extracted three times with ether, the organic phase is shaken with brine, dried on sodium sulfate and concentrated by evaporation in a vacuum. The residue is chromatographed on silica gel. With hexane/ether (8+2), 1.3 g of the alcohol is obtained as colorless oil.

IR: 3610, 2930, 2860, 1725, 1374, 1451, 993, 836 cm$^{-1}$.

For acetylation, 2.1 g of acetic anhydride is added to a solution of 1.82 g of the above-described alcohol in 5.1 ml of pyridine and stirred for 22 hours at room temperature. Then, it is concentrated by evaporation in a vacuum while adding toluene and the residue is chromatographed on silica gel. With hexane/ether (9+1), 1.83 g of the acetate is obtained as colorless oil.

IR: 2930, 2860, 1728, 1608, 1375, 1255, 993, 840 cm$^{-1}$.

For silylether cleavage, 1.85 g of the above-produced acetate in 113 ml of tetrahydrofuran is stirred with 3.1 g of tetrabutylammonium fluoride for 20 minutes at 0° C. and for 4 hours at 24° C. under argon. Then, it is diluted with ether, washed three times with water, dried on magnesium sulfate and concentrated by evaporation in a vacuum. The residue is chromatographed with ether/hexane (8+2) on silica gel. In this way, 1.3 g of the 1-alcohol is obtained as colorless oil.

IR: 3620, 3500, 2930, 2860, 1725, 1608, 1375, 1250, 990 cm$^{-1}$.

For oxidation of the 1-hydroxy group, 7.2 g of Collins reagent is added to 1.25 g of the above-produced alcohol in 71 ml of methylene chloride and stirred for 20 minutes at 0° C. Then, it is diluted with a mixture of hexane/ether (1+1), Celite is added, filtered, washed with hexane/ether (1+1) and concentrated by evaporation in a vacuum. The thus obtained 1-aldehyde is immediately used without further purification.

2.3 ml of Jones reagent (J. Chem. Soc. 1953, 2555) is instilled in a solution of 1.1 g of the above-produced aldehyde in 40 ml of acetone with stirring at −25° C. and stirred for 15 minutes at −25° C. under argon. Then, 8 ml of isopropanol is added, stirred for 5 minutes, diluted with 300 ml of ether, shaken twice with brine, dried on sodium sulfate and concentrated by evaporation in a vacuum. The residue is chromatographed on silica gel. With ether/hexane (7+3), 681 mg of the title compound is obtained as colorless oil.

IR: 3520 (broad), 2930, 2859, 1725, 1373, 1250, 990, 948 cm$^{-1}$.

The initial material for the above title compound is produced as follows:

5a) cis-(1RS)-1-Formyl-(2RS)-2-E(1E,3E)-(5RS)-5-acetoxy-1,3-tridecadienyl]-cyclopentane Diastereomer polar (12)

7.73 g of tetrabutylammonium fluoride is added to a solution of 3.68 g of (5RS)-5-acetoxy-1-[cis-1-(tert-butyl-dimethylsilyloxymethyl)-cyclopent-2-yl]-(1E,-3E)-tridecadiene (polar diastereomer), produced according to example 1d, in 360 ml of tetrahydrofuran at 0° C., stirred for 30 minutes at 0° C. and for 5 hours at 24° C. Then, it is diluted with 1 liter of ether and washed three times with brine. It is dried on magnesium sulfate, concentrated by evaporation in a vacuum and the residue is chromatographed on silica gel. With hexane/ether (7+3), 2.3 g of the alcohol is eluted as colorless oil.

IR: 3620, 3450, 2930, 2860, 1725, 1250, 991 cm$^{-1}$.

14 g of Collins reagent (chromic acid-pyridine complex) is added to a solution of 1.8 g of the above-produced alcohol in 56 ml of methylene chloride at 0° C. and stirred for 20 minutes at 0° C. Then, it is diluted with a mixture of hexane/ether (1+1), Celite is added, filtered and concentrated by evaporation in a vacuum. The thus obtained aldehyde was used without further purification.

IR: 2930, 2860, 1720, 1250, 991 cm$^{-1}$.

Example 6

(+/−)-(5RS)-5-Hydroxy-5-[cis-(2RS)-2-((1E,3E)-(5RS)-5-hydroxy-1,3-tridecadienyl)-(1RS)-Cyclopentyl]-pentanoic acid Diastereomer polar (12)

Analogously to example 2, 174 mg of the title compound is obtained from 360 mg of the diacetate, produced according to example 5, as colorless oil.

IR: 3400, 2930, 2855, 1723, 1360, 1230, 995, 930 cm$^{-1}$.

Example 7

(+/−)-(5RS)-5-Acetoxy-5-[cis-(2RS)-2,((1S,3E)-(5RS)-5-hydroxy-1,3-tridecadienyl)-(1RS)-cyclopentyl]-pentanoic acid Diastereomer polar (12)

Analogously to example 3, 238 mg of the title compound is obtained from 305 mg of the diacetate, produced according to example 5, as colorless oil.

IR: 3520, 2930, 2860, 1723, 1250, 990, 962 cm$^{-1}$.

Example 8

(+/−)-(5RS)-5-Hydroxy-5-[cis-(2RS)-2-((1E,3E)-(5RS)-5-hydroxy-1,3-tridecadienyl)-(1RS)-cyclopentyl]-pentan-1-ol Diastereomer polar (12)

Analogously to example 4, 115 mg of the title compound is obtained from 190 mg of the diacetate (intermediate product with the hydroxy group in 1-position), produced according to example 5, as colorless oil.

IR: 3600, 3380 (broad), 2930, 2860, 992 cm$^{-1}$.

Example 9

(+/−)-(5RS)-5-Acetoxy-5-[trans-(2RS,2-((1E,3E)-(5RS)-5-acetoxy-1,3-tridecadienyl)-1,3-tridecadienyl)-(1RS)-cyclopentyl]pentanoic acid Diastereomer A A solution of 22.3 g of 4-chloro-1-(tert-butyldimethylsilyloxy)-butane in 20 ml of tetrahydrofuran is instilled in 4.87 g of magnesium at 25° C. under argon, a crystal of iodine is added, heated for 10 minutes to 70° C., stirred for 30 minutes at 25° C. and diluted with 62.5 ml of tetrahydrofuran.

A solution of 8.1 g of trans-(1RS)-1-formyl-(2RS)-2-[(1E,3E)-(5RS)-5-acetoxy-1,3-tridecadienyl]-cyclopentane in 27 ml of tetrahydrofuran is instilled in 48.3 ml of the above magnesium-organic solution at −70° C. under argon and stirred for 1.5 hours at −70° C. It is mixed with 200 ml of saturated ammonium chloride solution, extracted with ether, the organic phase is shaken with brine, dried on sodium sulfate and concentrated by evaporation in a vacuum. The residue is chromatographed on silica gel with hexane/ethyl acetate (85+15). 8.2 g of the alcohol is obtained as colorless oil.

IR: 3450, 2930, 2860, 1725, 1374, 1255, 993, 840 cm$^{-1}$.

For acetylation, 8.6 ml of acetic anhydride is added to a solution of 7.85 g of the above-produced alcohol in 50 ml of pyridine and stirred for 21 hours at room temperature. Then, it is concentrated by evaporation in a vacuum while adding toluene and the residue is chromatographed on silica gel with hexane/ethyl acetate (85+15). 7.6 g of the acetate is obtained as colorless oil.

IR: 2940, 2862, 1728, 1375, 1257, 992, 840 cm$^{-1}$.

For silylether cleavage, 7.55 g of the above-produced acetate in 500 ml of tetrahydrofuran is stirred with 12.7 g of tetrabutylammonium fluoride for 1 hour at 0° and for 4 hours at 24° C. under argon. Then, it is diluted with ether, washed three times with water, dried on magnesium sulfate and concentrated by evaporation in a vacuum. The residue is chromatographed on silica gel. With hexane/ethyl acetate mixtures, 1.7 g of the nonpolar diastereomeric alcohol (diastereomer A) and 2.3 g of the polar diastereomer alcohol (diastereomer B) are obtained by multiple chromatographies as colorless oil.

IR (nonpolar alcohol): 3630, 3500, 2938, 2862, 1727, 1660, 1378, 1255, 992, 950 cm$^{-1}$.

IR (polar alcohol): 3620, 3480, 2938, 2862, 1726, 1660, 1378, 1255, 992, 950 cm$^{-1}$.

For oxidation of the 1-hydroxy group, 10.7 g of Collins reagent is added to 1.55 g of the above-produced nonpolar alcohol (diastereomer A) in 122 ml of methylene chloride at 0° C. and stirred for 20 minutes at 0° C. Then, it is diluted with a mixture of hexane/ether (1+1), Celite is added, filtered, washed with hexane/ether (1+1) and concentrated by evaporation in a vacuum. The thus obtained 1-aldehyde is immediately used without further purification.

3.3 ml of Jones reagent (J. Chem. Soc. 1953, 2555) is instilled in a solution of 1.57 g of the above-produced aldehyde in 58 ml of acetone with stirring at −25° C. and stirred for 15 minutes at −25° C. under argon. Then, 11.5 ml of isopropanol is added, stirred for 5 minutes, diluted with 400 ml of ether, shaken twice with brine, dried on sodium sulfate and concentrated by evaporation in a vacuum. The residue is chromatographed on silica gel. With hexane/ethyl acetate (6+4), 1.2 g of the title compound is obtained as colorless oil.

IR: 3520, 2930, 2860, 1725, 1658, 1360, 1250, 990, 946 cm$^{-1}$.

The initial material for the above title compound is produced as follows:

9a)

5-(trans-1-(tert-Butyl-dimethylsilyloxymethyl)-cyclopent-2-yl]-(2E,4E),pentadienoic acid ethyl ester 3.4 ml of concentrated sulfuric acid is added to a solution of 25 g of trans-cyclopentane-1,2-dicarboxylic acid in 64 ml of methanol and refluxed for 14 hours. Then, the excess alcohol is distilled off, the residue is poured on ice water, extracted four times with ether and the organic phase is washed with sodium bicarbonate solution and water. It is dried with sodium sulfate, concentrated by evaporation in a vacuum and the residue is distilled in a vacuum at 25 mtorr. At 56° C., 27 g of trans-cyclopentane-1,2-dicarboxylic acid dimethyl ester is obtained as colorless liquid.

IR: 2955, 2873, 1725, 1435 cm$^{-1}$.

230 ml of a 1.2 molar solution of diisobutylaluminum hydride in toluene is instilled in a solution of 13 g of trans-cyclopentane-1,2-dicarboxylic acid dimethyl ester in 300 ml of toluene at 0° C. under argon and stirred for 2 hours at 0° C. Then, 20 ml of isopropanol is instilled, stirred for 5 minutes, 116 ml of water is instilled and stirred for 2 hours at 22° C. It is filtered, washed with methylene chloride and concentrated by evaporation in a vacuum. The residue is purified by chromatography on silica gel. With ethyl acetate, 8 g of trans-1,2-dihydroxy-cyclopentane is obtained as colorless liquid.

IR: 3610, 3400, 2960, 1062 cm$^{-1}$.

17.1 g of imidazole and 18.9 g of tert-butyldimethylsilyl chloride are added to a solution of 16 g of trans-1,2-dihydroxymethyl-cyclopentane in 146 ml of dimethylformamide at 0° C. and stirred for 22 hours at 24° C. It is diluted with 1.6 l of ether, shaken twice with 80 ml of 10% sulfuric acid each, washed neutral with water, dried on magnesium sulfate and concentrated by evaporation in a vacuum. The residue is chromatographed on silica gel. With hexane/ethyl acetate (9+1), 12 g of trans-1-(tert-butyldimethylsilyloxymethyl)-2-hydroxymethyl-cyclopentane is obtained as colorless liquid.

IR: 3400, 2960, 2860, 1260, 840 cm$^{-1}$.

70 g of Collins reagent (chromic acid-pyridine complex) is added to a solution of 14.4 g of the above-described monosilylether in 750 ml of methylene chloride and stirred for 30 minutes at 0° C. Then, it is diluted with a mixture of hexane/ether (3+2), Celite is added, filtered and concentrated by evaporation in a vacuum. 14 g of the aldehyde is obtained, which is used without further purification.

IR: 2958, 2860, 2720, 1719, 840 cm$^{-1}$.

For Wittig-Horner olefination, 16.1 g of phosphonocrotonic acid triethyl ester and 9.8 g of diazabicycloundecene (DBU) are added at 24° C. to a stirred suspension of 2.7 g of lithium chloride in 536 ml of acetonitrile and stirred for 10 minutes. Then, a solution of 13 g of the above-described aldehyde in 107 ml of acetonitrile is instilled for 3.5 hours at 24° C. and then diluted with ether. It is shaken in succession with water, 10% citric acid solution and water, dried on magnesium sulfate and concentrated by evaporation in a vacuum. The residue is chromatographed with hexane/ethyl acetate on silica gel. In this way, 11 g of the title compound is obtained as colorless oil.

IR: 2958, 2860, 1705, 1640, 1620, 1470, 1255, 1000, 838 cm$^{-1}$.

9b)

5-[trans-1-(tert-Butyl-dimethylsilyloxymethyl)-cyclopent-2-yl]-(2E,4E)-pentadien-1-al 50 ml of a 1.2 molar solution of diisobutylaluminum hydride in toluene is instilled in a solution of 9.8 g of ester, produced according to example 9a, in 250 ml of toluene at −70° C. under argon and stirred for 30 minutes at −70° C. Then, 10 ml of isopropanol and, after 5 minutes, 30 ml of water are instilled, stirred for 2.5 hours at 23° C., filtered, washed with methylene chloride and concentrated by evaporation in a vacuum. The residue is purified by chromatography on silica gel. With hexane/ether (7+3), 7.6 g of the alcohol is obtained as colorless oil.

IR: 3610, 3450, 990, 940, 840 cm$^{-1}$.

For aldehyde production, a solution of 7.5 g of the above-produced alcohol in 250 ml of toluene is mixed with 22 g of manganese dioxide and stirred for 4 hours at 24° C. Then, it is filtered, concentrated by evaporation and chromatographed on silica gel. With hexane/ethyl acetate (8+2), 7.4 g of the title compound is obtained as colorless oil.

IR: 2960, 2860, 2740, 1682, 1638, 988, 940, 840 cm$^{-1}$.

9c)

(5-RS)-5-Acetoxy-1-[trans-1-(tert-butyl-dimethylsilyloxymethyl)-cyclopent-2-yl]-1-(1E,3E)-tridecadiene A solution of 17.8 g of octyl bromide in 24 ml of ether is instilled in 2.24 g of magnesium in 12 ml of ether with heating and stirred for 30 minutes at 25° C. A solution of 7.4 g of aldehyde, produced according to example 9b, in 130 ml of ether is instilled in 16.4 ml (=30.1 mmol) of this Grignard solution at −20° C. under argon and stirred for 45 minutes at −20° C. It is mixed with saturated ammonium chloride solution, extracted three times with ether, the organic phase is shaken with brine, dried on sodium sulfate and concentrated by evaporation in a vacuum. The residue is chromatographed on silica gel. With hexane/ethyl acetate (7+3), 8.6 g of alcohol (diastereomer mixture) is obtained as colorless oil.

For acetylation, 12.5 ml of acetic anhydride is added to a solution of 8.5 g of the above-produced alcohol in 85 ml of pyridine and stirred for 23 hours at room temperature. Then, it is concentrated by evaporation in a vacuum while adding toluene and the residue is chromatographed on silica gel. With hexane/ethyl acetate (97+3), 8.6 g of the title compound is obtained as colorless oil.

IR: 2938, 2860, 1725, 1657, 1255, 993, 945, 840 cm$^{-1}$.

9d)

trans-(1RS)-1-Formyl-(2RS)-2-[1E,3E)-(5RS)-5-acetoxy-1,3-tridecadienyl]-cyclopentane 19.9 g of tetrabutylammonium fluoride is added to a solution of 9.1 g of the acetate, produced according to example 9c, in 900 ml of tetrahydrofuran at 0° C., stirred for 15 minutes at 0° C. and for 4 hours at 24° C. Then, it is diluted with 2 l of ether and washed three times with brine. It is dried with sodium sulfate, concentrated by evaporation in a vacuum and the residue is chromatographed on silica gel. With hexane/ethyl acetate (7+3), 7.18 g of the alcohol is eluted as colorless oil.

IR: 3620, 3450, 2938, 2862, 1730, 1255, 995 cm$^{-1}$.

63 g of Collins reagent (chromic acid-pyridine complex) is added to a solution of 8.1 g of the above-produced alcohol in 250 ml of methylene chloride at 0° C. and stirred for 20 minutes at 0° C. Then, it is diluted with a mixture of hexane/ether (1+1), Celite is added, filtered and concentrated by evaporation in a vacuum. The thus obtained aldehyde was used without further purification.

IR: 2930, 2860, 2731, 1721, 1250, 990 cm$^{-1}$.

Example 10

(+/−)-(5RS)-5-Hydroxy-5-[trans-(2-RS)-2-(1E,3E)-(5RS)-5-hydroxy-1,3-tridecadienyl)-(1RS)-cyclopentyl]-pentanoic acid Diastereomer A Analogously to example 2, 168 mg of the title compound is obtained from 250 mg of the diacetate, produced according to example 9, as colorless oil.

IR (film): 3400, 2930, 2858, 1715, 1660, 1250, 989, 930 cm$^{-1}$.

Example 11

(+/−)-(5RS)-5-Acetoxy-5-[trans-(2RS)-2-(1E,3E)-(5RS)-5-hydroxy-1,3-tridecadienyl)-(1RS)-cyclopentyl]-pentanoic acid Diastereomer A Analogously to example 3, 204 mg of the title compound is obtained from 250 mg of the diacetate, produced according to example 9, as colorless oil.

IR (film): 3450, 2930, 2860, 1736, 1713, 1660, 1245, 990 cm$^{-1}$.

Example 12

(+/−)-(5RS)-5-Acetoxy-5-[trans-(2RS)-2-(1E,3E)-(5RS)-5-acetoxy-1,3-tridecadienyl)-(1RS)-cyclopentyl]-pentanoic acid Diastereomer B 15 g of Collins reagent is added to a solution of 2.2 g of the polar alcohol (diastereomer B), produced in example 9, in 173 ml of methylene chloride at 0° C. and stirred for 20 minutes at 0° C. Then, it is diluted with a mixture of hexane/ether (1+1), Celite is added, filtered, washed with hexane/ether (1+1) and concentrated by evaporation in a vacuum. The thus obtained 1-aldehyde is immediately used without further purification.

4.7 ml of Jones reagent is instilled in a solution of 2.25 g of the above-produced aldehyde in 83 ml of acetone with stirring at −25° C. and stirred for 12 minutes at −25° C. under argon. Then, 16.5 ml of isopropanol is added, stirred for 5 minutes, diluted with ether, shaken with brine, dried on sodium sulfate and concentrated by evaporation in a vacuum. The residue is chromatographed on silica gel. With hexane/ethyl acetate (6+4), 1.6 g of the title compound is obtained as colorless oil.

IR: 3620, 2930, 2860, 1721, 1658, 1370, 1250, 989, 946 cm$^{-1}$.

Example 13

(+/−)-(5RS)-5-Hydroxy-5-[trans-(2RS)-2-(1E,3E)-(5S)-5-hydroxy-1,3-tridecadienyl)-(1RS)-cyclopentyl]-pentanoic acid Diastereomer B Analogously to example 2, 178 mg of the title compound is obtained from 250 mg of the diacetate, produced according to example 12, as colorless oil.

IR: 3600, 3420, 2930, 2859, 1730, 1660, 1250, 990 cm$^{-1}$.

Example 14

(+/−)-C₅RS)-5-Acetoxy-5-[trans-(2RS)-2-(1E,3E)-(5S)-5-hydroxy-1,3-tridecadienyl)-(1RS)-cyclopentyl]-pentanoic acid Diastereomer B Analogously to example 3, 187 mg of the title compound is obtained from 250 mg of the diacetate, produced according to example 12, as colorless oil.

IR (film): 3450, 2925, 2850, 1730, 1708, 1660, 1245, 985 cm$^{-1}$.

Example 15

(+/−)-(5RS)-5-Hydroxy-5-[cis-(2RS)-2-)1E,3E)-(5S)-5-hydroxy-1,3-tridecadienyl)-(1RS)-cyclopentyl]-pentanoic acid methyl ester Diastereomer nonpolar (12)

An ethereal diazomethane solution is instilled in a solution of 85 mg of the acid, produced according to example 2, in 8 ml of methylene chloride at 0° C. until permanent yellow coloring and stirred for 15 minutes at 0° C. Then, it is concentrated by evaporation in a vacuum and the residue is chromatographed on silica gel. With hexane/ethyl acetate (2+8), 69 mg of the title compound is obtained as colorless oil.

IR (film): 3600, 2925, 2855, 1738, 1658, 990 cm$^{-1}$.

Example 16

(+/−)-(5RS)-5-Hydroxy-5-[cis-(2RS)-2-(1E,3E)-(5S)-5-hydroxy-1,3-tridecadienyl)-(1RS)-cyclopentyl]-pentanoic acid methyl ester Diastereomer polar (12)

Analogously to example 15, 102 mg of the title compound is obtained from 120 mg of the acid, produced according to example 6, as oil.

IR (film): 3610, 2925, 2855, 1737, 1660, 990 cm$^{-1}$.

Example 17

(+/−)-(5RS)-5-Acetoxy-5-[cis-(2RS)-2-(1E,3E)-(5S)-5-hydroxy-1,3-tridecadienyl)-(1RS)-cyclopentyl]-pentanoic acid methyl ester Diastereomer polar (12)

Analogously to example 15, 71 mg of the title compound is obtained from 80 mg of the acid, produced according to example 7, as colorless oil.

IR (film): 3400, 2924, 2858, 1739, 1658, 1240, 990 cm$^{-1}$.

Example 18

(+/−)-(5RS)-5-Hydroxy-5,[cis-(2RS)-2-(1E,3E)-(5S)-5-hydroxy-1,3-tridecadienyl-(1RS)-cyclopentyl]-pentanoic acid-tris-(hydroxymethyl)-aminomethane salt Diastereomer polar (12)

A solution of 15 mg of tris-(hydroxymethyl)-aminomethane in 0.03 ml of water is added to a solution of 40 mg of the carboxylic acid, produced according to example 6, in 6 ml of acetonitrile at 70° C. It is allowed to cool with stirring, is decanted after 16 hours from the solvent and the residue is dried in a vacuum. 14 mg of the title compound is isolated as waxy mass.

Example 19

(+/−)-(5RS)-5-Hydroxy-5-[cis-(2RS)-2-(1E,3E)-(5S)-5-hydroxy-1,3-tridecadienyl)-(1RS)-cyclopentyl]-pentanoic acid-1,5-lactone Diastereomer polar (12)

0.5 g of anhydrous magnesium sulfate is added to a solution of 27 mg of the carboxylic acid, produced according to example 6, in 5 ml of toluene at 24° C. over a period of 24 hours in portions and stirred for another 24 hours at 24° C. Then, it is filtered and the evaporation residue is chromatographed on silica gel. With toluene/ethyl acetate (7+3), 14 mg of the 1,5-lactone is eluted as colorless oil.

IR: 3600, 2930, 2860, 1728, 1250, 990 cm$^{-1}$.

We claim:

1. Leukotriene-$B_4$ derivatives of formula I

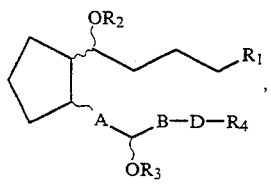

(I)

in which $R^1$ is $CH_2OH$, $CH_3$, $CF_3$, $COOR^5$, or $CONR^6R^7$, or $R^1$ together $R^2$ is a carbonyl group;

$R^2$ and $R^3$ are the same or different and are H or an organic carboxylic acid or sulfonic acid radical with 1-15C atoms selected from aliphatic, cycloaliphatic, aromatic, aromatic aliphatic, and heterocyclic radicals, optionally substituted independent from one another by $C_{1-4}$-alkyl, hydroxy, $C_{1-4}$-alkoxy, amino, or oxo groups or fluorine, chlorine, or bromine atoms;

$R^4$ is H, $(C_{1-10})$-alkyl, optionally substituted by chlorine or bromine; $C_{3-10}$-cycloalkyl, optionally substituted by $C_{1-4}$-alkyl groups; a $C_{6-10}$-aryl radical, optionally substituted, independent from one another, by 1-3 chlorine or bromine atoms, a phenyl group, 1-3 $C_{1-4}$-alkyl groups, a $C_{1-4}$-alkoxy group, a fluoromethyl group, a chloromethyl group, a trifluoromethyl group, a carboxyl group, or a hydroxy group; or a 5-6-member heterocyclic ring;

$R^5$ is hydrogen; $C_{1-10}$-alkyl, optionally substituted by halogen atoms, $C_{1-2}$-alkoxy, $C_{6-10}$-aryl, di-$C_{1-4}$-alkylamino, tri-$C_{1-4}$-alkylammonium; $C_{3-10}$-cycloalkyl, optionally substituted by a $C_{1-4}$-alkyl group; a $C_{6-10}$-aryl radical, optionally substituted by 1-3 chlorine or bromine atoms, a phenyl group, 1-3 $C_{1-4}$-alkyl groups, a $C_{1-4}$-alkoxy group, a fluoromethyl group, a chloromethyl group, a trifluoromethyl group, a carboxyl group, or a hydroxy group; $CH_2$-$CO$-$(C_6$-$C_{10})$-aryl; or a 5-6-member heterocyclic ring;

A is a trans-, trans-$CH=CH$—$CH=CH$, a $CH_2CH_2$—$CH=CH$— or a tetramethylene group;

B is a $C_{1-10}$-straight-chain or branched-chain alkylene group, which optionally can be substituted by fluorine or the group

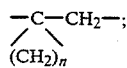

D is a direct bond, oxygen, sulfur, —C≡C—, —CH=$CR^8$ or, together with B, can also be a direct bond;

$R^6$ and $R^7$ are the same or different and are H or $C_{1-4}$-alkyl or $R^7$ is H and $R^6$ is $C_{1-10}$-alkanoyl or $C_{1-10}$-alkanesulfonyl;

$R^8$ is H, $C_{1-5}$-alkyl, chlorine, or bromine; and n is 3-5 and, if $R^5$ is hydrogen, their salts with physiologically compatible bases and their cyclodextrin clathrates.

2. A leukotriene-$B_4$ derivative of claim 1, wherein $R^1$ is $CH_2OH$ or $COOR^5$, and $R^5$ is hydrogen, $C_{1-10}$-alkyl, $C_{5-6}$-cycloalkyl, or phenyl optionally substituted by 1 or 2 chlorine, bromine, phenyl, $C_{1-4}$-alkyl, $C_{1-4}$-alkoxy, chloromethyl, fluoromethyl, trifluoromethyl, carboxy, or hydroxy.

3. A leukotriene-$B_4$ derivative of claim 1, wherein A is a trans-, trans-$CH=CH$—$CH=CH$, or a tetramethylene group.

4. A leukotriene-$B_4$ derivative of claim 1, wherein $R^2$ and $R^3$ are the same or different and are H or a carboxylic acid radical with 1-15C atoms.

5. A leukotriene-$B_4$ derivative of claim 1, wherein $R^4$ is H, $C_{1-10}$-alkyl, $C_{5-6}$-cycloalkyl, or phenyl optionally substituted by 1 or 2 chlorine, bromine, phenyl, $C_{1-4}$-alkyl, $C_{1-4}$-alkoxy, chloromethyl, fluoromethyl, trifluoromethyl, carboxy, or hydroxy.

6. A leukotriene-$B_4$ derivative of claim 1, wherein $CH_2OH$ or $COOR^5$; $R^5$ is H or $C_{1-4}$-alkyl; A is trans-, trans-$CH=CH$—$CH=CH$, or a tetramethylene group; B is a straight- or branched-chain alkyl with up to 5 carbon atoms; $R^2$ and $R^3$ are the same or different and mean H or a $C_{1-6}$-carboxylic acid radical; $R^1$ and $R^2$ are a carbonyl; and $R^4$ is H or $C_{1-10}$-alkyl.

7. A derivative selected from the group consisting of:

(+/−)-(5RS)-5-acetoxy-5-[cis-(2RS)-2-((1E,3E)-(5RS)-5-acetoxy-1,3-tridecadienyl)-(1RS)-cyclopentyl]-pentanoic acid;

(+/−)-(5RS)-5-hydroxy-5-[cis-(2RS)-2-((1E,3E)-(5RS)-5-hydroxy-1,3-tridecadienyl)-(1RS)-cyclopentyl]-pentanoic acid;

(+/−)-(5RS)-5-acetoxy-5-[cis-(2RS)-2-((1E,3E)-(5RS)-5-hydroxy-1,3-tridecadienyl)-(1RS)-cyclopentyl]-pentanoic acid;

(+/−)-(5RS)-5-hydroxy-5-[cis-(2RS)-2-((1E,3E)-5-hydroxy-1,3-tridecadienyl)-(1RS)-cyclopentyl]-pentan-1-ol;

(+/−)-(5RS)-5-acetoxy-5-[trans-(2RS)-2-((1E,3E)-(5RS)-5-acetoxy-1,3-tridecadienyl)-(1RS)-cyclopentyl]-pentanoic acid;

(+/−)-(5RS)-5-hydroxy-5-[trans-(2RS)-2-(1E,3E)-(5S)-5-hydroxy-1,3-tridecadienyl)-(1RS)-cyclopentyl]-pentanoic acid;

(+/−)-(5RS)-5-hydroxy-5-[cis-(2RS)-2-(1E,3E)-(5S)-5-hydroxy-1,3-tridecadienyl)-(1RS)-cyclopentyl]-pentanoic acid methyl ester;

(+/−)-(5RS)-5-acetoxy-5-[cis-(2RS)-2-(1E,3E)-(5S)-5-hydroxy-1,3-tridecadienyl)-(1RS)-cyclopentyl]-pentanoic acid methyl ester;

(+/−)-(5RS)-5-hydroxy-5-[cis-(2RS)-2-(1E,3E)-(5S)-5-hydroxy-1,3-tridecadienyl)-(1RS)-cyclopentyl]-pentanoic acid-tris-(hydroxymethyl)-aminomethane salt; and (+/−)-(5RS)-5-hydroxy-5-[cis-(2RS)-2-(1E,3E)-(5S)-5-hydroxy-1,3-tridecadienyl)-(1RS)-cyclopentyl]-pentanoic acid-1,5-lactone.

8. Pharmaceutical preparations which contain one or more compounds according to claim 1.

* * * * *